United States Patent [19]

Schmukler

[11] Patent Number: 5,283,194
[45] Date of Patent: Feb. 1, 1994

[54] APPARATUS AND METHODS FOR ELECTROPORATION AND ELECTROFUSION

[76] Inventor: Robert E. Schmukler, 13905 Vista Dr., Rockville, Md. 20853

[21] Appl. No.: 913,612

[22] Filed: Jul. 16, 1992

Related U.S. Application Data

[62] Division of Ser. No. 733,854, Jul. 22, 1991, Pat. No. 5,173,158.

[51] Int. Cl.⁵ .................. C12N 13/00; C12N 15/00; C12N 15/02; C12N 15/87
[52] U.S. Cl. .................. 435/287; 435/172.2; 435/173.6; 935/52; 935/85; 935/89; 935/93
[58] Field of Search .................. 435/287, 173, 172.2; 935/93, 89, 85, 52

[56] References Cited

U.S. PATENT DOCUMENTS

| | | | |
|---|---|---|---|
| 3,870,617 | 3/1975 | Bourat et al. | 204/301 |
| 4,081,340 | 3/1978 | Zimmermann et al. | 204/299 R X |
| 4,289,756 | 9/1981 | Zimmermann et al. | 424/533 |
| 4,441,972 | 4/1984 | Pohl | 935/93 X |
| 4,578,167 | 3/1986 | Schoner | 435/287 X |
| 4,578,168 | 3/1986 | Hofmann | 435/287 X |
| 4,661,451 | 4/1987 | Hansen | 435/287 |
| 4,663,292 | 5/1987 | Wong et al. | 435/287 |
| 4,800,163 | 1/1989 | Hibi et al. | 435/173.6 X |
| 4,804,450 | 2/1989 | Mochizuki et al. | 435/173.6 X |
| 4,822,470 | 4/1989 | Chang | 435/172.2 |
| 4,832,814 | 5/1989 | Root | 435/287 X |
| 4,849,089 | 7/1989 | Marshall, III | 435/287 X |
| 4,849,355 | 7/1989 | Wong | 435/173.6 |
| 4,894,343 | 1/1990 | Tanaka et al. | 435/301 |
| 4,906,576 | 3/1990 | Marshall, III | 435/287 |
| 4,910,140 | 3/1990 | Dower | 435/172.3 |
| 4,923,814 | 5/1990 | Marshall, III | 435/173.6 |

FOREIGN PATENT DOCUMENTS

| | | | |
|---|---|---|---|
| 208637 | 1/1987 | European Pat. Off. | |
| 3505147 | 10/1986 | Fed. Rep. of Germany | 435/172.2 |
| 63-084477 | 4/1988 | Japan | 435/287 |
| 1-141582 | 6/1989 | Japan | 435/287 |

OTHER PUBLICATIONS

Schmukler, "Measurements of the Electrical Impedance of Living Cells In the Frequency Domain", Charge and Field Effects in Biosystems-2, 357-372 (1989).
Schmukler, et al., "A New Transient Technique For Measurement of Isolated Cell Impedance", Proceedings of the Tenth Annual Northeast Bio-engineering Conference 213-216 (Mar. 1982).
Schmukler, et al., "A Transient Impedance Approach to Nonfaradaic Electrochemical Kinetics at Living Cell Membranes", Journal of the Electrochemical Society: Electrochemical Science and Technology 526-528 (Mar. 1982).
Sale, A. J., et al. "Effects of High Electric Fields on Micro-Organisms/III Lysis of Erythrocytes and Protoplasts", Biochimica et Biophysica Acts. 37-43 (1968).
Zimmermann, W. "Electric Field-Mediated Fusion and Related Electrical Phenomena", Biochimica et Biophysica Acta 694, pp. 227-277 (1982).

Primary Examiner—John Niebling
Assistant Examiner—John S. Starsiak, Jr.
Attorney, Agent, or Firm—Finnegan, Henderson, Farabow, Garrett & Dunner

[57] ABSTRACT

An insulating film in a container has pores whose diameter is smaller than the diameter of a first type of cells in the container. The first type of cells are trapped in the pores, so that when an electric field is applied to the container, electroporation of the first type of cells occurs. If a second type of cells, smaller than the first type of cells, are also trapped in the pores, electrofusion will occur between the first and second types of cells trapped in the same pores.

8 Claims, 3 Drawing Sheets

APPARATUS AND METHODS FOR ELECTROPORATION AND ELECTROFUSION

This is a division of application Ser. No. 07/733,854, filed Jul. 22, 1991, now U.S. Pat. No. 5,173,158.

BACKGROUND OF THE INVENTION

This invention relates generally to the fields of electroporation and electrofusion, and more specifically to electroporation and electrofusion using low level electric fields.

Electroporation involves the opening of the cell membrane, usually to allow genetic or other material to pass into or out of the cell. When genes are employed, this activity is known as genetic transfection.

Electrofusion, or cell-cell joining, involves the fusion of membranes of different cells after their membranes have been opened by electroporation. Electrofusion is used to form new cells (hybridomas) with unique properties, or to genetically reprogram existing cells such as for plant breeding or genetic engineering.

Conventional methods of opening cell membranes for transfection or cell fusion use inactivated viruses or chemicals such as polyethylene glycol (PEG). These techniques have certain disadvantages. Strict controls are needed in the case of viral transfection to prevent unwanted contamination. Also there are problems with unwanted biologic responses. Furthermore the chemical side effects of PEG transfection or fusion can adversely affect cellular viability.

Electric-field induced fusion, or electrofusion, has shown promising results. In electrofusion, different types of cells are placed in close contact by applying non-uniform alternating current electric fields to a solution of those cells. The electric fields cause dielectrophoresis, which in turn causes cells to move to a region of highest field intensity and organize into formations of variable length.

Once close cell-to-cell membrane contact is achieved, fusion occurs by subjecting the cells to one or more pulses of high intensity electric fields. The high intensity fields first cause reversible electric breakdown in the zone of contact between the two cells, and then fusion of the two cells occurs.

This process, however, also has some drawbacks. Conventional electrofusion employs an unnatural chemical environment in the low conductivity solutions. Also, some conventional electrofusion produces random electrofusion because of the use of cell suspensions. In electrofusing cells A & B, the resulting fused cells could be composed of A:A, B:B, A:A:B, A:B:B, etc., as well as the desired result of simply A:B.

It is therefore an object of this invention to provide methods and apparatus for electroporation and electrofusion which yield more predictable results than conventional methods.

Another object of this invention is to provide methods and apparatus for electroporation and electrofusion which minimize damage caused to the cells.

II. SUMMARY OF THE INVENTION

To achieve the objects of this invention, a method of electroporation of a first type of cells is provided by placing the first type of cells in a solution held by a container in which an insulating film divides the container into two portions. The film is penetrated by pores whose diameter is smaller than the diameter of the first type of cells. Next, the first type of cells are trapped in different ones of the pores so that a portion of each of the trapped cells extends into the different one of the pores. Finally, an electric field is applied to the container to cause electroporation of the trapped first type of cells.

A method of electrofusion of a first type of cells with a second type of cells according to this invention, where the first type of cells are larger than the second type of cells, comprises the steps of placing the first type of cells in a solution held by a container across which is placed an insulating film penetrated by pores whose diameter is smaller than the diameter of the first type of cells; causing the first type of cells to be trapped in a different ones of the pores such that a portion of each of the trapped first cells extends into a different one of the pores, the trapped cells extending into a portion of the pores on a first side of the insulating film; placing the second type of cells in the container; causing trapped ones of the second type of cells to enter certain ones of the pores of the insulating film side into which trapped first type of cells extend and to contact trapped first type of cells, the trapped second type of cells entering the certain pores from a second side of the insulating film; and applying an electric field to the container to cause electrofusion of the ones first type of cells and second type of cells which are in the same pores in contact with one another.

The accompanying drawings, which are incorporated in and which constitute a part of this specification, illustrate an implementation of this invention and, together with the accompanying textual description, explain the principles of the invention.

III. BRIEF DESCRIPTION OF THE DRAWINGS

IV. DESCRIPTION OF THE PREFERRED EMBODIMENT

Reference will now be made in detail to a preferred embodiment of this invention illustrated in the accompanying drawings.

Figure 1:
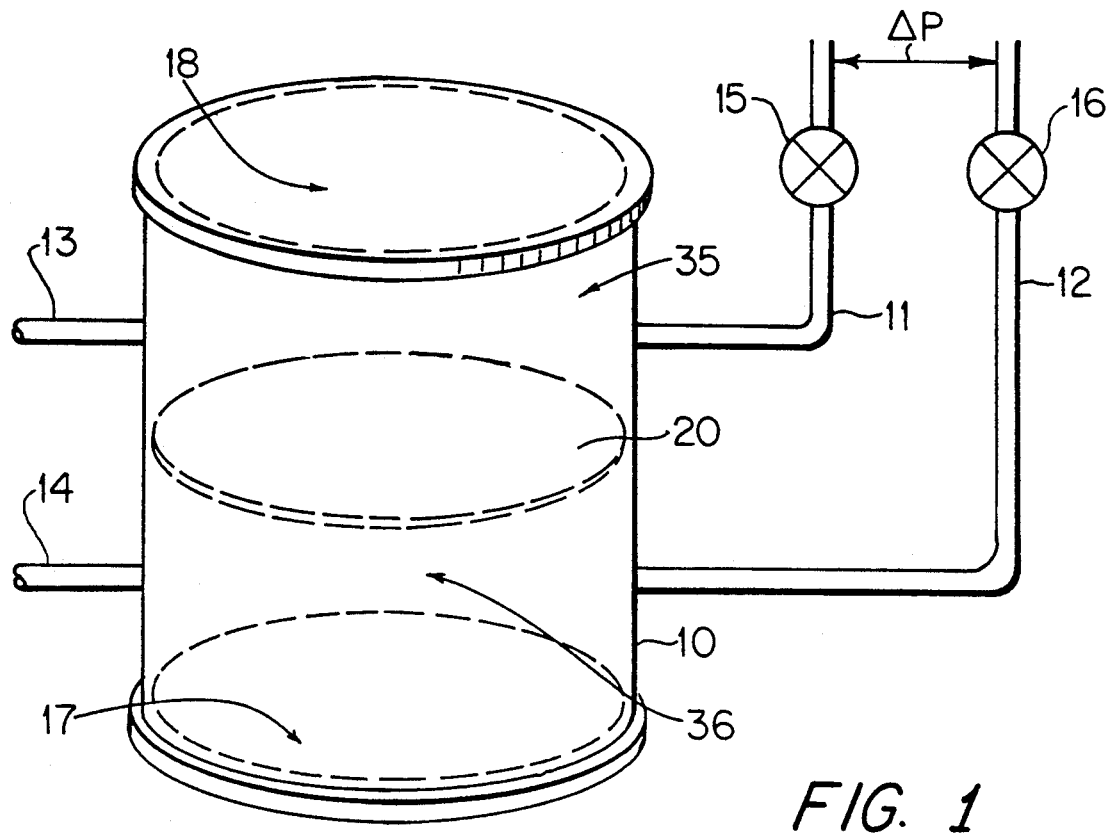
FIG. 1 is a diagram of a preferred embodiment of the invention.

FIG. 1 is a diagram of a preferred apparatus according to the present invention. In FIG. 1, a container 10 includes an insulating film 20 which is placed across container 10 at about container 10's midpoint to divide container 10 into two portions 35 and 36. The exact location of insulated film 20 in container 10 is not critical, however, nor is its shape, as explained below. Preferably insulating film is extremely thin, on the order of 10-15 microns with a pore density around $4 \times 10^5$ pores/cm$^2$. Such filters are commercially available, such as the Nuclepore filter manufactured by Costar Corporation of Cambridge, Massachusetts.

Figure 2:
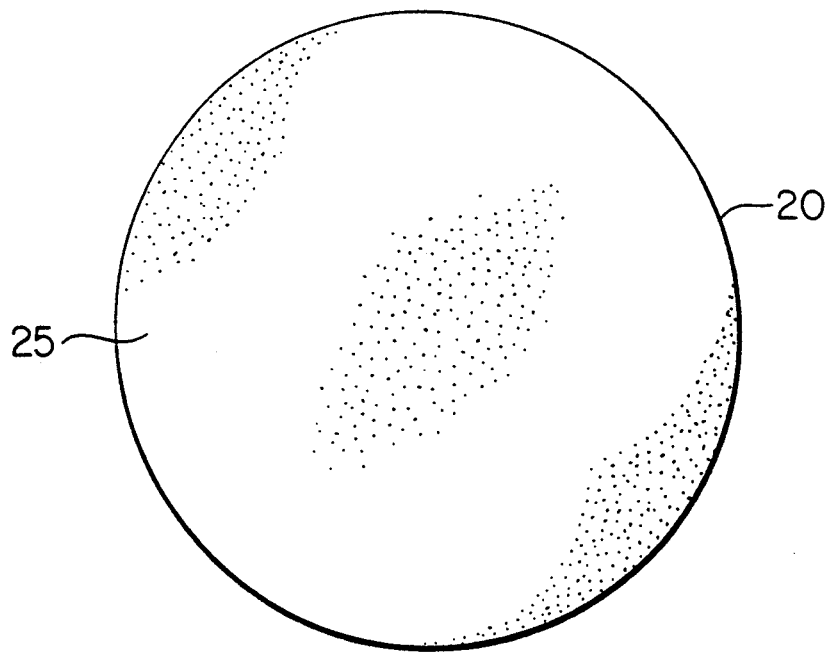
FIG. 2 is a top view of the insulating film shown in FIG. 1.

Insulating film 20 is penetrated by several pores, as can be seen in FIG. 2, which is a top view of film 20.

Pores 25 are distributed throughout film 20 either randomly, as in FIG. 2, or in some type of order.

For electroporation or electrofusion according to the invention, a first type of cells, such as myeloma cells, are placed into portion 35 of the container 10. Although the following discussion refers to cells, the invention operates with cell nuclei also. The cells are preferably suspended in either a low conductivity solution containing sugar, such as mannitol or sorbitol, or a high conductivity solution, such a Ringers solution or tissue culture media.

Figure 3:
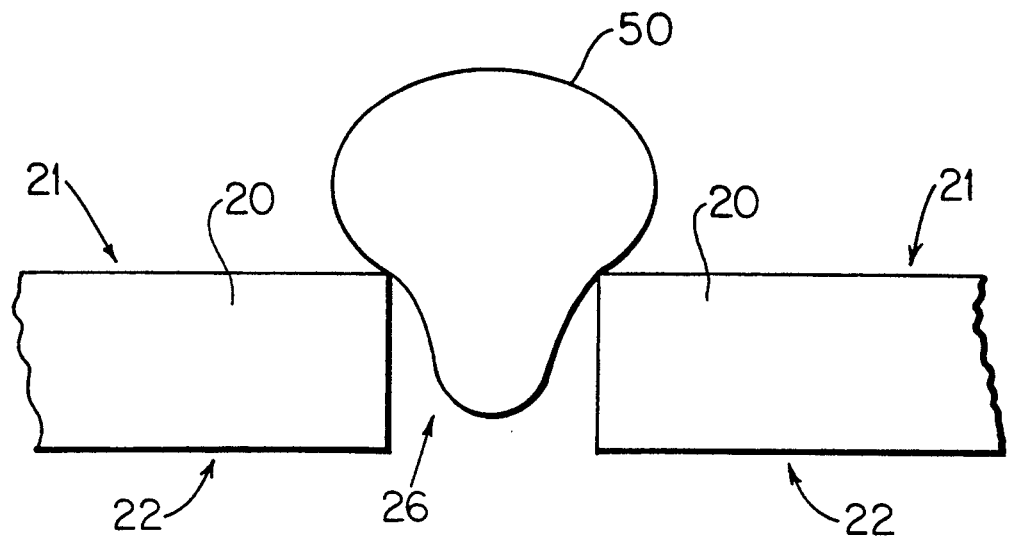
FIG. 3 shows an insulating film with one type of cells trapped within a pore.

The size of pores 25 should be chosen so that the diameter of the pores is smaller than the diameter of the first type of cells, but large enough to allow the first type of cells to be trapped in the pores, as illustrated in FIG. 3. FIG. 3 shows a cutaway view of a cell 50 trapped in pore 26 of film 20 such that a portion of cell 50 extends substantially into pore 26 from a first side 21 of insulating film 20. The relative sizes of pores 25 and 26 and the first type of cells ensures that the first type of cells will become trapped in the pores as shown in FIG. 3.

The first type of cells can be trapped in pores 25 of film 20 by pressure, such as by using a hydrostatic pressure head from a regulated pressure source (not shown) or a vacuum source (not shown) supplied by lines 11 and 12. The cells can also be trapped by letting the cells settle into pores 25 by gravity or by placing container 10 in a centrifuge.

Once the first type of cells are trapped, a low voltage pulse is applied to the solution via electrodes 18 and 19 which are located on opposite sides of container 10. That pulse generates an electric field in the solution which causes electroporation of the portions of those cells which extend into pores 25. A preferred magnitude of the voltage pulse is on the order of one to twenty-five volts.

After electroporation occurs, changes in the pressure across film 20 cause the cells either to expel materials into the solution on the second side 22 of the insulating film 20, or to pull in such materials. The ingress or egress of material for each cell takes place through the electroporated hole in the cell wall.

When the pressure gradient across insulating film 20 is positive (i.e. is higher in portion 35 than in portion 36), the contents of the trapped first type of cells are expelled. When the pressure gradient across the film is negative, or decreases from a positive value, the trapped first type of cells will pull in material, such as genetic material (DNA), from portion 36. Lymphocytes, or isolated nuclei will be too large to be pulled in through the electroporated membrane, but can be brought into more intimate contact with the first type of cells by pressure manipulation. The ingress or egress of material takes place through the electroporated holes in the cells' walls. By coordinating the timing of any pressure changes with the pulses which cause electroporation, the amount of material passing into out of the trapped cells can be controlled.

Once the first type of cells are trapped in the pores of the insulating film 20, electrofusion can occur by introducing a second type of cell or cell nuclei into portion 36 of container 10 (FIG. 1), and causing the second cells to move towards the second side 22 of film 20 and contact ones of the trapped first type of cells in pores 25.

Figure 4:
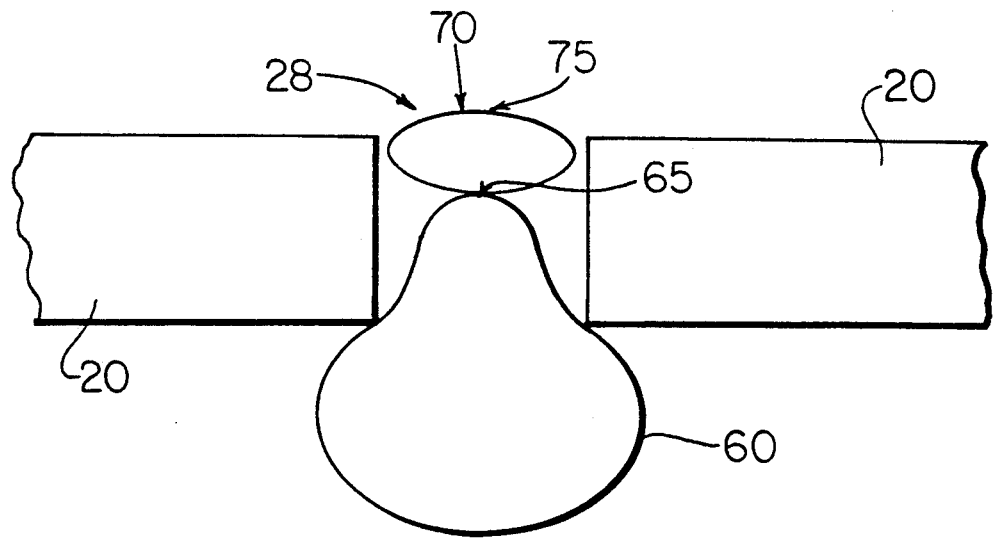
FIG. 4 shows an insulating film with two kinds of cells trapped within a pore.

For electrofusion, the size of pores 25 in film 20 should be selected so that the proper amount of secondary material, or a single second cell or cell nucleus, can enter a pore in film 20 and be properly oriented adjacent to trapped cell type 1. FIG. 4 shows insulating film 20 with a portion of a first type of cell 60 being trapped inside pore 28, and a second type of cell 70 also being trapped inside pore 28 adjacent to cell 60. When a pulse of one to twenty-five volts is applied to insulating film 20, both cell 60 and cell 70 electroporate at a location 65 where both cells contact. Electrofusion will then occur within the channel of pore 28 of insulating film 20 when the field from the pulse is removed. It is important to insure that the size of pore 20 is only large enough to fit a single small second type of cell so that only one of each type of cell is involved in electrofusion.

When the second type of cell 70 electroporates, a second hole can be formed at location 75 if cell 70 is small enough to fit entirely within the pore. This hole will close by itself, however, when a reversible electroporation electric field is used. Persons of ordinary skill in the art will recognize that poration is reversible below certain energy levels (pulse width and pulse height).

Figure 5:
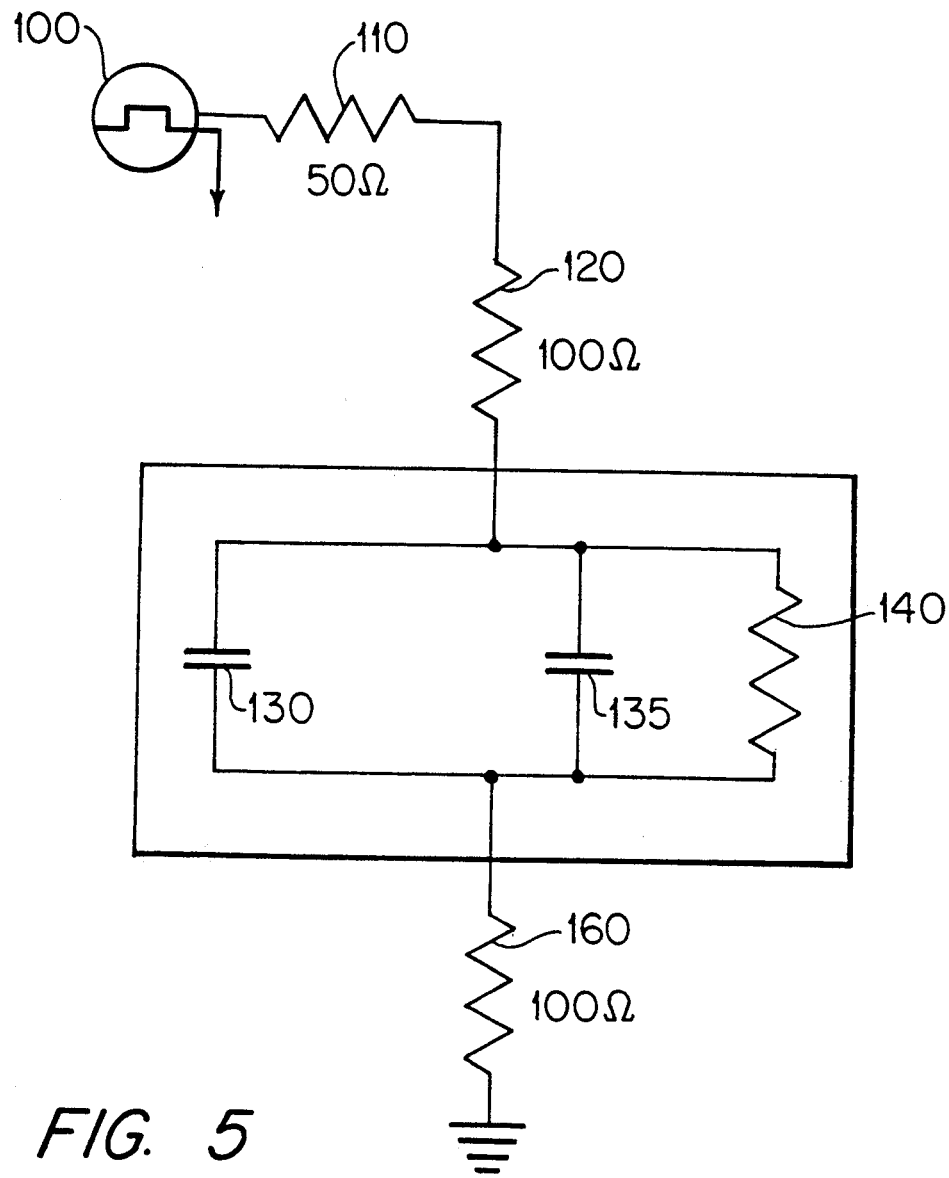
FIG. 5 shows a circuit diagram illustrating the operation of the electric fields on the preferred embodiment of this invention.

FIG. 5 shows an equivalent circuit diagram which illustrates the operation of the electrical fields in the preferred embodiment of this invention. In FIG. 5, there is a source 100 of an electrical field which has an impedance 115 of 50 ohms. That is coupled to insulating film 20 by another impedance 120 of 100 ohms representing the resistance due to the electrolyte column (i.e., Riungers Solution) above the insulating film.

Insulating film 20 with cells embedded includes a filter capacitance 130, a cell membrane capacitance 135, and a leakage resistance 140 around the pores of film 20. Capacitance 135 represents the cell membrane capacitance of the trapped cell. There is another 100 ohm resistance 160 in the path to ground representing the resistance of the Ringer's electrolyte column below the insulating film.

For a leakage resistance of 150 ohms, the total resistance seen by load generator 110 will be 400 ohms when the filter capacitance 130 and the cell membrane capacitance 135 are fully charged. The voltage drop across the insulating film 20 will then be 150/400 V, where V is the voltage of generator 110. If V is 10 volts, then the voltage across the filter will be 3.75 volts. For a filter with a thickness of 10 microns, the voltage gradient would be 3.75 volts/10 microns or 3750 volts/centimeter.

One advantage of this invention is that the heating caused by the fields is minimal. If load generator 110 generates 10 volts, the current will be only 10 volts/400 ohms or 0.025A. The heating due to that current, $I^2R$, equals $(0.025A)^2$ (400 ohms) or 0.25 watts. This figure, however, is the total power dissipated by the entire circuit. The power dissipation across the filter of the cells is only $(0.25A)^2$ (150 ohms) or 0.094 watts. Such heating can be kept from harming the cells or material by the heat capacity of the solution itself or, if necessary, by either water jackets or outside cooling.

Preferably, the method of this invention is carried out by filling portion 35 of container 10 with a solution of the first type of cells to trap a sufficient number of the first type of cells within the pores 25 of insulating film 20. Container 10 is then inverted, ensuring that a hydrostatic pressure is applied sufficient to keep the trapped first type of cells in the pores. The secondary material, such as the second type of cells, is then introduced into the portion 36 of container 10, and gravity will force the second type of materials into the pores 25 which already contain first type of cells. Application of the appropriate electric field then causes the electroporation and electrofusion as described above other methods, such as those discussed above, may also be used to trap the first and second type of cells.

Preferably, container 10 can be made using materials such as polycarbonate pipe, and insulating film 20 can be made using a track-etched polycarbonate filter which is glued inside of the pipe. Container 10 is connected to lines 11, 12, 13, and 14 (FIG. 1) via appropriate fittings. As explained above, lines 11 and 12 are connected to a pressure source (not shown) such as a pump. Lines 13 and 14 allow the infusion of cells or secondary material. Stopcocks 15 and 16 in lines 11 and 12, respectively, control pressure difference between lines 11 and 12, and thereby control the pressure in container 10.

Electrofusion takes place because the increasing current flux through the pores produces an electrical field gradient whose strength is between 0.8 and 3Kv/cm which is necessary to electroporate the cellular wall. Because the only portions of the cell which experience the higher voltage gradients are inside of a pore of the insulating film 20, only those portions are electroporated.

An advantage of this invention is that the use of lower voltages for electroporation, coupled with the use of porous electrodes, can greatly reduce electrolysis. This is because it is possible to couple entirely by electrode capacitance, and the electrodes are not directly adjacent to the cells. To reduce electrolysis further, the electrodes used to apply the fields should be made of metals, such as tantalum, or titanium, carbon or other inert materials.

Figure 6:
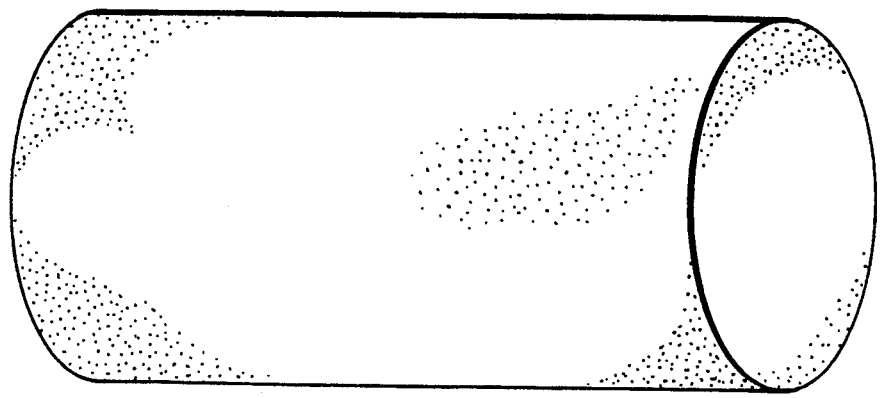
FIG. 6 shows a different shape for an insulating film according to this invention.

Persons of ordinary skill will recognize that modifications and variations may be made to this invention without departing from the spirit and scope of the general inventive concept. For example, insulating film 20 could be tubular, such as shown in FIG. 6. Such a film would be useful in a bioreactor. This invention in its broader aspects is therefore not limited to the specific details or representative methods shown and described.

What is claimed:

1. An apparatus for electroporation of a first type of cells comprising:
   a container;
   an insulating film, penetrated by pores, dividing the container into two sections;
   a first type of cells in a solution in one of the sections, the diameter of the first type of cells being larger than the diameter of the pores;
   means for causing the first type of cells to become trapped in different ones of the pores such that a portion of each of the trapped first type of cells extends into a different one of the pores; and
   means for applying a low voltage electric field of less than 25 volts to the container to pass through the two sections and the pores to create a substantially larger voltage gradient across the trapped cells than across the remainder of the container to cause electroporation of the trapped first type of cells at the portions which extend into the pores.

2. The apparatus of claim 1 wherein the means for applying an electric field to the container includes electrodes placed on opposite side of the container.

3. The apparatus of claim 1 wherein the insulating film is flat.

4. An apparatus for electrofusion of a first type of with a second type of cells which are smaller than the first type of cells comprising:
   a container containing an insulating film, penetrated by pores, which divides the container into two sections;
   a first type of cells in a solution in one section of the container, the diameter of the first type of cells being larger than the diameter of the pores;
   means for causing the first type of cells to become trapped in different ones of the pores such that a portion of each of the trapped first type of cells extends into a different one of the pores;
   a second type of cells in the other section of the container;
   means for causing trapped ones of the second type of cells to enter from a second side of the insulating film ones of the pores of the insulating film into which trapped first type of cells extend and to contact trapped first type of cells; and
   means for applying an electric field to pass through both of sections of the container and the pores to cause electroporation of the first type of cells at the portions which are trapped in the pores and to cause electroporation of the second type of cells in the pores, and then to cause electrofusion of the trapped first type of cells and the trapped second type of cells which are in the same ones of the pores and in contact with each other.

5. The apparatus of claim 4 wherein the means for causing the first type of cells to become trapped in different ones of the pores includes
   lines for introducing a pressure into the container to draw the first type of cells into the pores.

6. The apparatus of claim 4 wherein the means for applying an electric field to the container includes
   electrodes placed on opposite side of the container.

7. The apparatus of claim 4 wherein the insulating film is flat.

8. An apparatus for electroporation of a first type of cells comprising:
   a container;
   an insulating film, penetrated by pores, dividing the container into two sections;
   a first type of cells in a solution in one of the sections, the diameter of the first type of cells being larger than the diameter of the pores;
   means for causing the first type of cells to become trapped in different ones of the pores such that a portion of each of the trapped first type of cells extends into a different one of the pores, the means for causing the first type of cells to become trapped including
   lines for introducing a pressure into the container to draw the first type of cells into the pores; and
   means for applying a low voltage electric field to the container to pass through the two sections and the pores to create a substantially larger voltage gradient across the trapped first type of cells than across the remainder of the container, thereby to cause electroporation of the trapped first type of cells at the portions which extend into the pores.

* * * * *

UNITED STATES PATENT AND TRADEMARK OFFICE
CERTIFICATE OF CORRECTION

PATENT NO. : 5,283,194
DATED : February 1, 1994
INVENTOR(S) : Robert E. Schmukler It is certified that error appears in the above-indentified patent and that said Letters Patent is hereby corrected as shown below:

On the Title page, item [54], and col. 1, lines 1-2 in the Title should read--APPARATUS FOR ELECTROPORATION AND ELECTROFUSION__ .

Signed and Sealed this

Seventeenth Day of May, 1994

Attest:

BRUCE LEHMAN

*Attesting Officer*     *Commissioner of Patents and Trademarks*